US00PP12239P2

(12) United States Plant Patent
Glicenstein

(10) Patent No.: US PP12,239 P2
(45) Date of Patent: Nov. 27, 2001

(54) CHRYSANTHEMUM PLANT NAMED 'YOVICKI'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/478,450

(22) Filed: Jan. 6, 2000

(51) Int. Cl.[7] ..... A01H 5/00
(52) U.S. Cl. ..... Plt./287
(58) Field of Search ..... Plt./287, 290, 289

(56) References Cited

U.S. PATENT DOCUMENTS

P.P. 5,326 * 11/1984 Meek et al. ..... Plt./290
P.P. 10,091 * 10/1997 Trees ..... Plt./318
P.P. 10,901 * 5/1999 VandenBerg ..... Plt./287
P.P. 11,830 * 4/2001 Fuess ..... Plt./287

OTHER PUBLICATIONS

UPOV–ROM, 2001/01, Plant Variety Database, GTI Jouve Retrieval Software, citation for 'Yovicky'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yovicki', characterized by its uniformly mounded plant habit; freely branching growth habit; dark green foliage; uniform flowering; decorative-type inflorescences that are about 5.4 cm in diameter; attractive golden bronze ray florets that are dark bronze when opening giving a bi-colored appearance to the inflorescence; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and hereinafter referred to by the cultivar name Yovicki.

The new cultivar is a product of a planned breeding program conducted by the Inventor in Salinas, Calif. and Alva, Fla. The objective of the breeding program is to create new garden-type Chrysanthemum cultivars having inflorescences with desirable inflorescence forms, attractive floret colors and good garden performance.

The new cultivar originated from a cross made by the Inventor in Salinas, Calif., in December, 1995, of the *Dendranthema grandiflora* cultivar Jean, disclosed in U.S. Plant Pat. No. 10,901, as the female, or seed, parent with an unidentified proprietary seedling selection as the male, or pollen, parent.

The cultivar Yovicki was discovered and selected by the Inventor as a flowering plant within the progency of the stated cross in a controlled environment in Alva, Fla. in November, 1996. The selection of this plant was based on its desirable inflorescence form, attractive ray floret color and excellent garden performance.

Asexual reproduction of the new cultivar by terminal cuttings taken in a controlled environment in Alva, Fla. has shown that the unique features of this new Chrysanthemum are stable and reproduced true to type in successive generations.

SUMMARY OF THE INVENTION

The cultivar Yovicki has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yovicki'. These characteristics in combination distinguish 'Yovicki' as a new and distinct cutivar:

1. Uniformly mounded plant habit.
2. Freely branching, dense, full plants.
3. Dark green foliage.
4. Uniform flowering.
5. Decorative-type inflorescences that are about 5.4 cm in diameter.
6. Attractive golden bronze ray florets that are dark bronze when opening giving a bi-colored appearance to the inflorescence.
7. Numerous inflorescences per plant.
8. Excellent garden performance with the blooms lasting at least three weeks.

Compared to plants of the parent cultivar, Jean, plants of the new Chrysanthemum are more uniformly mounded, flower about one week later under natural season conditions, and differ in ray floret color as plants of the cultivar Jean have light pink-colored ray florets.

Plants of the new Chrysanthemum are similar to the cultivar Viking, disclosed in U.S. Plant Pat No. 5,326. However in side-by-side comparisons under commercial practice, plants of the new Chrysanthemum are more uniformly mounded and flower more uniformly than plants of the cultivar Viking.

Plants of the new Chrysanthemum can also be compared to the cultivar Empire Harmony, disclosed in U.S. Plant Pat. No. 11,830. However in side-by-side comparisons under commercial practice, plants of the new Chrysanthemum differ from plants of the cultivar Empire Harmony in the following characteristics:

1. Plants of the new Chrysanthemum are slightly larger than plants of the cultivar Empire Harmony.
2. Plants of the new Chrysanthemum have larger and darker green leaves than plants of the cultivar Empire Harmony.
3. Plants of the new Chrysanthemum have larger inflorescences than plants of the cultivar Empire Harmony.
4. Ray floret color of plants of the new Chrysanthemum is richer bronze than ray floret color of the cultivar Empire Harmony.
5. Plants of the new Chrysanthemum flower about one week earlier than plants of the cultivar Empire Harmony under natural season photoperiodic conditions.

BRIEF DESCRIPTION OF THE PHOTOGRAPH

The accompanying photograph illustrates the overall appearance of the new Chrysanthemum. The photograph shows the colors as true as it is reasonably possible to obtain in colored reproductions of this type. Colors in the photograph may differ slightly from the color values cited in the detailed botanical description which more accurately describe the actual colors of the new Chrysanthemum. The photograph comprises a top perspective view of a typical flowering plant of 'Yovicki'.

DETAILED BOTANICAL DESCRIPTION

In the following description, color references are made to The Royal Horticultural Society Colour Chart except where general terms of ordinary dictionary significance are used. The following observations and measurements describe plants grown in Pendleton, S.C., under conditions which approximate those generally used in commercial garden Chrysanthemum production. One rooted cutting was planted in a 15-cm container on Jul. 26, 1999 and plants were grown under natural season conditions. Plants were not pinched, that is, the terminal apex was not removed to enhance branching. Measurements and numerical values represent averages for typical flowering plants.

Botanical classification: *Dendranthema grandiflora* cultivar Yovicki.

Commercial classification: Decorative-type garden chrysanthemum.

Parentage:

*Female parent.*—*Dendranthema grandiflora* cultivar Jean, disclosed in U.S. Plant Pat. No. 10,901.

*Male parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle; mounded plant form. Stems initially upright, then outwardly spreading giving a uniformly mounded appearance to the plant. Freely branching with lateral branches potentially developing at every node.

*Plant height.*—About 23 cm.

*Plant spread.*—About 31 cm.

*Stems.*—Texture: Pubescent. Color: Slightly darker than 146A.

*Foliage description.*—Leaf arrangement: Alternate. Length: About 5.2 cm. Width: About 4.2 cm. Apex: Cuspidate. Base: Attenuate. Margin: Palmately lobed, sinuses parallel to divergent. Texture: Upper surface sparsely pubescent; lower surface moderately pubescent. Veins prominent on lower surface. Petiole length: About 1.5 cm. Petiole diameter: About 3 mm. Color: Young foliage upper surface: Darker than 147A. Young foliage lower surface: 147B. Mature foliage upper surface: Darker than 147A. Mature foliage lower surface: Close to 147B. Venation upper surface: 147A. Venation lower surface: 147B.

Inflorescence description:

*Appearance.*—Decorative-type inflorescence form with elongated oblong to spatulate-shaped ray florets. Inflorescences borne on terminals above foliage, arising from leaf axils. Disk and ray florets arranged acropetally on a capitulum. About 115 inflorescences per plant.

*Flowering response.*—Under natural season conditions, plants flower in the autumn about 69 days after planting.

*Inflorescence bud.*—Height: About 6 mm. Diameter: About 7 mm. Color: Between 146A and 147A.

*Inflorescence size.*—Diameter: About 5.4 cm. Depth (height): About 1.8 cm. Diameter of disc: About 5 mm.

*Ray florets.*—Shape: Elongated oblong to spatulate; concave. Length: About 2.4 cm. Width: About 7.5 mm. Apex: Minutely dentate. Margin: Entire. Texture: Smooth, glabrous, satiny. Orientation: Initially upright, then perpendicular to the peduncle. Number of ray florets per inflorescence: About 262. Color: When opening, upper surface: Toward apex, 183A; toward base, golden yellow, 17A to 12A. When opening, lower surface: Toward apex, 183A; toward base, golden yellow, 17A to 17C to 12A. Opened inflorescence, upper surface: Close to 17A to 15A to 12A. Opened inflorescence, lower surface: Close to 15A to 12A.

*Disc florets.*—Shape: Tubular, apex dentate. Length: About 6 mm. Width: Apex: About 1.5 mm. Base: About 1 mm. Number of disc florets per inflorescence: About 20. Color: Immature: Close to 151A. Mature: Apex: 12A. Mid-section: Whitish green. Base: White.

*Peduncle.*—Aspect: Flexible, angled about 55 to 60° to the stem. Length: First peduncle: About 6.3 cm. Third peduncle: About 7.8 cm. Diameter: About 2 mm. Texture: Pubescent. Color: Between 146A and 147A.

*Reproductive organs.*—Androecium: Present on disc florets only. Anther color: 14A. Pollen: Moderate. Pollen color: 17A. Gynoecium: Present on both ray and disc florets.

*Seed.*—Seed production has not been observed.

Disease resistance: Plants of the new Chrysanthemum have not been shown to be resistant to pathogens common to Chrysanthemums.

It is claimed:

1. A new and distinct cultivar of Chrysanthemum plant named 'Yovicki', as illustrated and described.

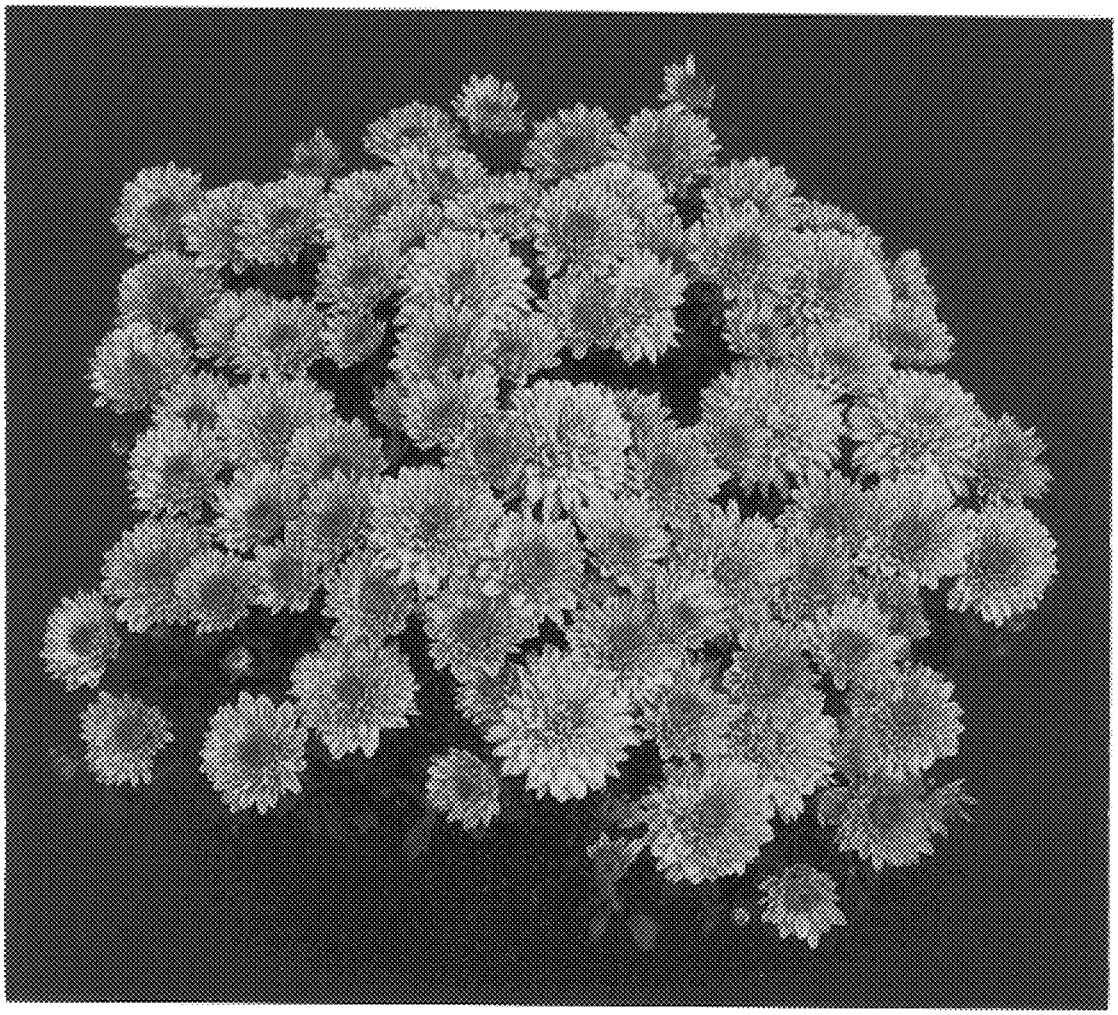

* * * * *